(12) United States Patent
Rosenkoetter

(10) Patent No.: US 6,265,435 B1
(45) Date of Patent: Jul. 24, 2001

(54) METHOD FOR ENHANCING CORNEAL PENETRATION BY WATER SOLUBLE OPHTHALMIC DRUGS

(76) Inventor: Hans Rosenkoetter, Schurthplatz #4, D79822 Titisee-Neustadt (DE)

(*) Notice: Subject to any disclaimer, the term of this patent is extended or adjusted under 35 U.S.C. 154(b) by 0 days.

(21) Appl. No.: 09/520,132

(22) Filed: Mar. 7, 2000

(51) Int. Cl.$^7$ ................................................. A61K 31/335
(52) U.S. Cl. ........................... 514/449; 514/603; 514/912
(58) Field of Search ..................... 514/603, 912, 514/449

(56) References Cited

U.S. PATENT DOCUMENTS

| | | | |
|---|---|---|---|
| 4,698,361 | 10/1987 | Di Schiena | 514/471 |
| 4,895,807 | 1/1990 | Cherksey | 436/63 |
| 5,182,258 | 1/1993 | Chiou | 514/3 |
| 5,221,696 | 6/1993 | Ke et al. | 514/786 |
| 5,227,372 | 7/1993 | Folkman | 514/58 |
| 5,258,374 | 11/1993 | Bianco | 514/158 |
| 5,585,401 | 12/1996 | Brandt et al. | 514/562 |
| 5,661,130 | 8/1997 | Meezan et al. | 514/25 |
| 5,763,491 | 6/1998 | Brandt et al. | 514/603 |
| 5,814,655 | 9/1998 | Patel et al. | 514/567 |

OTHER PUBLICATIONS

Current Eye Research, vol. 4 No. 4, 1985 "Transport Processes Across the Rabbit Corneal Epithelium" by Klyce & Crosson.

Journal of Membrane Biology, 66, 133–144, "Effects of At$^+$ on Ion Transport by Corneal Epithelium of the Rabbit", by Klyce & Marshall.

Journal of Membrane Biology, 95, 229–240, 1987 "Intracellular Ion Concentrations in the Frog Corneal Epithelium During Stimulation and Inhibition of Ion Secretion" by Roger Rick et al.

Primary Examiner—Zohreh Fay
(74) Attorney, Agent, or Firm—John F. Bryan

(57) ABSTRACT

A loop diuretic is applied topically to the corneal epithelium along with a therapeutic ophthalmic drug in an aqueous solution. The loop diuretic acts to temporarily block the discrete ion channels for outward $Na^+2Cl^-K^+$ cotransport through the baso-lateral membrane of the corneal epithelium while allowing inward ion movement, to the anterior chamber unaffected and thus serves to enhance the rate of diffusion of the ophthalmic drug through the cornea to the interior of the eye through solvent drag.

16 Claims, 2 Drawing Sheets

US 6,265,435 B1

METHOD FOR ENHANCING CORNEAL PENETRATION BY WATER SOLUBLE OPHTHALMIC DRUGS

FIELD OF THE INVENTION

The present invention relates to the field of ophthalmic drug delivery and more particularly, to enhanced penetration of corneal membranes of the eye by water soluble therapeutic agents.

BACKGROUND OF THE INVENTION

In order for an ophthalmic drug to be therapeutically effective, it is generally necessary for the drug to penetrate the cornea, where it may be taken up in the aqueous humor and other tissues in the inner eye. Drugs or drug products which act on the exterior surface of the cornea for treating dryness or irritation. Thus, the treatment of physiological conditions within the eye requires the movement of topically applied ophthalmic drugs through the cornea.

To pass through the cornea, a drug must penetrate three layers of tissue, namely, the epithelium, stroma and endothelium. Lipid soluble compounds more easily penetrate such membrane barriers that are rich in lipids, while water soluble compounds more easily penetrate water rich membrane barriers. The epithelial and endothelial cell membranes are relatively lipid rich, while the stroma has a relatively high water content. Since topically applied drugs must penetrate these differently structured barriers, it would appear that an ideal drug compound should be both lipid and water soluble.

The stroma and endothelium together are approximately 360 microns thick and these layers allow penetration by aqueous solutions through a process of inter-cellular diffusion. There is no particular need for enhancing the aqueous diffusion rate through the stroma or endothelium, since the epithelium is the only operative barrier to aqueous penetration of the cornea. Therefore, enhanced penetration of topically applied aqueous drugs through the corneal epithelium would proportionately increase the total drug dosage absorbed into the eye as is obviously desirable.

Prior to the present invention, there have been attempts to enhance the penetration of drugs through the corneal epithelium to an optimal point at which the stroma alone controls drug transport through the cornea. These attempts have included use of chemical agents to enhance drug penetration of the epithelium. It has been reported that benzalkonium chloride (BAC), bile salts, dimethyl sulfoxide (DMSO), ethylenediamine tetraacetate (EDTA) and 1-dodecylazayl-cycloheptan-2-one (AZONE<<)enhance the corneal penetration of certain drugs. The following publications may be referred to for further background concerning the use of such agents to enhance corneal penetration: *Acta Ophthalmological*, Vol. 53, p. 365 (1975); *J. Phar. Pharmacol.* Vol. 39, p. 124 (1987); *Chem. Abstracts*, Vol. 106, 125934t, p. 402 (1987); *Journal of Pharmaceutical Sciences*, Vol. 77, No. 1 (January, 1988); and *Investigative Ophthalmology and Visual Science*, Vol. 29, No. 2 (February, 1988). Notwithstanding such prior attempts, there continues to be a need for a means of safely and effectively enhancing the penetration of the cornea by ophthalmic drugs in aqueous solution.

A first object of the present invention therefore, is to provide an improved rate of epithelium penetration by topical ophthalmic drugs in aqueous solution. A second object is that this improved penetration rate be achieved in a completely safe manner, without ocular irritation or other undesirable side effects. A third object is that methods of the present invention be simple and readily accomplished without the need of clinical oversight.

SUMMARY OF THE INVENTION

The present inventions contemplate a unique utilization of electrochemical mechanisms for penetration of the epithelium by ophthalmic drugs in aqueous solution. Practice of the present inventions uses some steps, compounds and apparatus well known in the biological and ophthalmological arts and therefore, not the subject of detailed discussion herein.

A topical loop diuretic applied to the corneal epithelium blocks outwardly directed ion movement of the $Na^+2Cl^-K^+$ cotransporter in the baso-lateral membrane so that the net inwardly directed ion movement is increased. In this circumstance, transport through the corneal epithelium of a topical ophthalmic drug in aqueous solution is facilitated by inwardly directed solvent drag. This enhancement of the transport rate through the corneal epithelium makes it more nearly consistent with the normal aqueous diffusion rate through the stroma and endothelium and increases total drug penetration of the cornea. Thus, the addition of a loop diuretic to an aqueous, non-ionic ophthalmic drug solution provides more efficient and more effective treatment for internal eye conditions in either clinical or non-clinical circumstances.

BRIEF DESCRIPTION OF THE DRAWINGS

The accompanying drawings are incorporated into and form a part of the specification to assist in explaining the present inventions. The drawings illustrate the functioning of the inventions and are not to be construed as limiting the inventions to only those examples illustrated and described. The various advantages and features of the present inventions will be apparent from a consideration of these drawings, which illustrate the membrane arrangement of the human eye and various aspects of membrane electrochemical processes as follows.

DETAILED DESCRIPTION OF THE DRAWINGS

Figure 1:
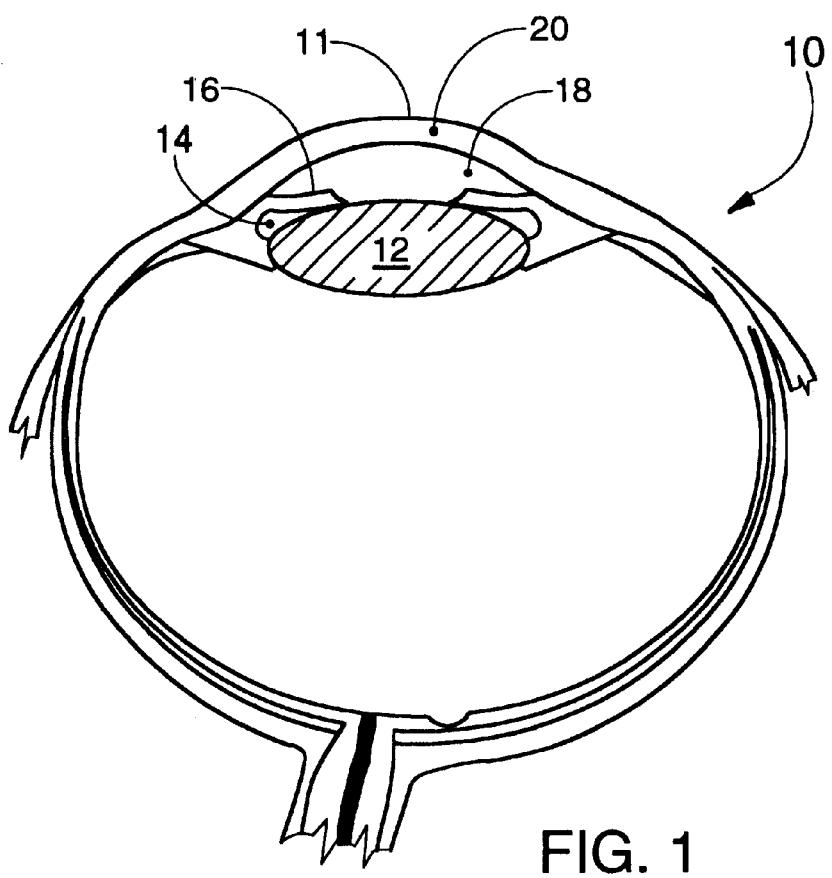
FIG. 1 shows a cross-sectional view of the human eye and cornea.

The present inventions are described in the following by referring to the drawings to show how the inventions function and how they can be practiced. In these drawings, reference characters are used throughout the views to indicate like or corresponding parts. The embodiments shown and described herein are exemplary. Many details are well knovin in the art, and as such are neither shown nor described. It is not claimed that all of the details, elements, or steps described and shown were invented herein. Even though numerous characteristics and advantages of the present inventions have been described in the drawings and accompanying text, the description is illustrative only, and changes may be made in the detail, especially in matters of the compounds used and the sequence of steps employed, within the principles of the inventions, to the full extent indicated by the broad general meaning of the terms used in the attached claims.

Figure 1A:
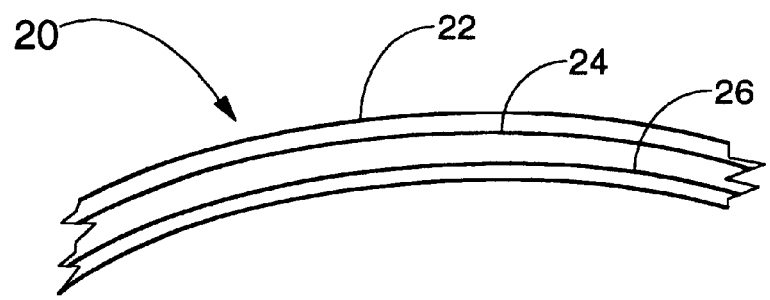

FIGS. 1 and 1A illustrate a simplified cross-sectional view of the human eye 10, normally wetted and protected by lacrimal film 11. Here it is seen that lens 12 resides in posterior chamber 14, behind iris 16 and anterior chamber 18, which in turn, is covered by cornea 20. Cornea 20 comprises three layers, the outer layer being the epithelium 22, the mid-layer being the stroma 24, and the inner layer, the endothelium 26. As previously mentioned, the stroma 24 and endothelium 26 are readily penetrable by aqueous solutions, while the epithelium 22 is the essential barrier thereto. Thus, the main subject of the present inventions is the corneal epithelium 22.

Figure 2:
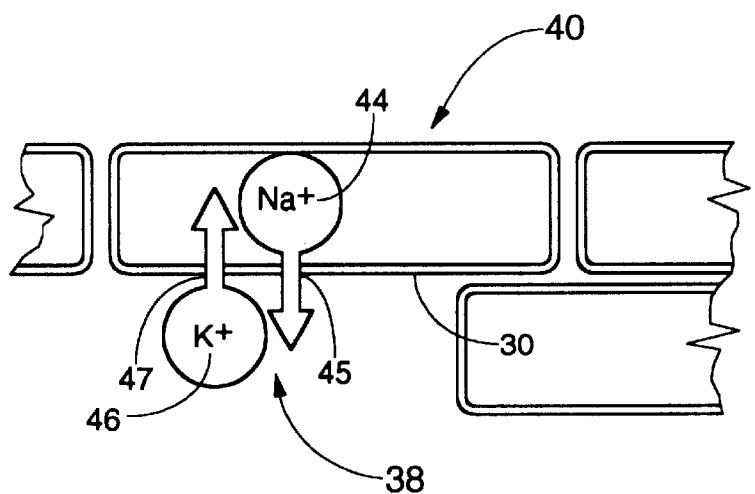
FIG. 2 illustrates the $Na^+K^+$ATPase aspect.
Figure 3:
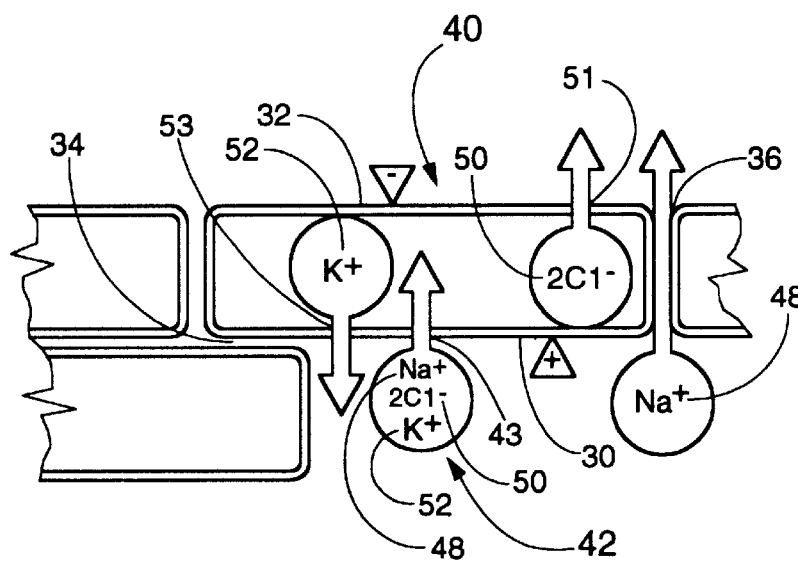
FIG. 3 illustrates the $Na^+2Cl^-K^+$ cotransporter aspect.
Figure 4:
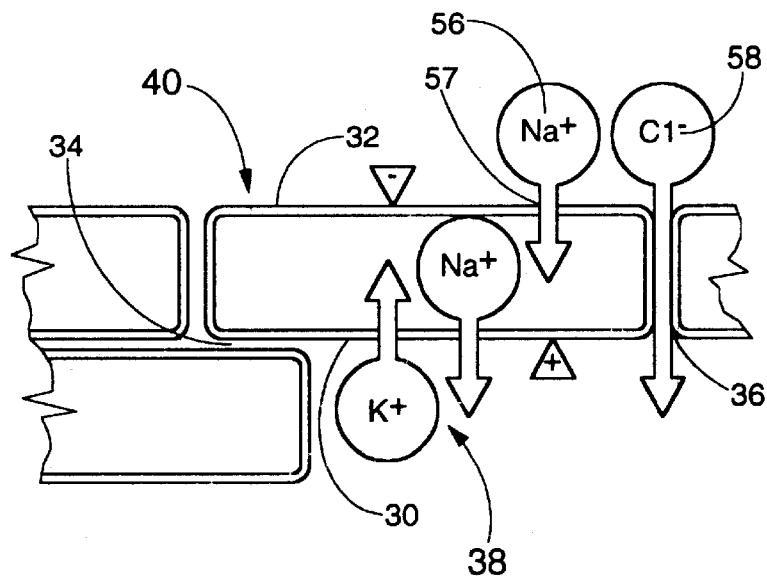
FIG. 4 illustrates the inwardly directed $Na^+$ transport aspect.

FIGS. 2–4 are schematic showings of electrochemical membrane processes and ion transports, but also illustrate structural details of the corneal epithelium 22. The corneal epithelium 22 consists of five to seven layers of squamous, or scale-like cells, tightly arranged in a delicate network. The extracellular spaces consist of longitudinal intercellular and transverse paracellular capillary spaces 34 and 36 respectively. Each cell 40 of corneal epithelium 22 has a baso-lateral membrane 30 and an apical membrane 32 in a polar relationship. The baso-lateral membranes 30 face inwardly, toward anterior chamber 18 of eye 10 and the apical membranes 32 face outwardly, toward the lacriminal film 11. $Cl^-$ ions migrate transcellularly from the baso-lateral membrane 30 side to the apical membrane 32 side, while $Na^+$ ions migrate oppositely from the apical membrane 32 side to the baso-lateral membrane 30 side. Ion transport takes place through certain cell wall membranes by way of ion channels, as shown below, which, when the cell reaches a given electrical charge condition, open to pass discrete ions. Membranes 30 and 32 have different physiological functions insofar as they relate to ion channels, but ion transports through discreet channels through cell wall membranes are well known to those skilled in the biochemical arts relating to muscle, kidney, bowel and excretory gland processes and hence, are not described in detail herein.

Lacrimal film 11, intercellular spaces 34 and paracellular spaces 36 contain an aqueous solution, with $Na^+$ and $Cl^-$ ions surrounded by a cloud of water molecules. In the normal state of corneal epithelium 22, the $Cl^-$ and $Na^+$ fluxes are nearly in balance. The net transport rate from one side of the epithelium 22 to the opposite side is considered to be the sum of transcellular and extracellular ion transports per unit of time.

FIG. 2 illustrates the well known $Na^+K^+ATPase$ pump 38 in baso-lateral membrane 30, showing the manner in which $Na^+$ ions 44, from inside of cell 40, transport to intercellular space 34 in a coupled exchange with $K^+$ ions 46 taken into cell 40. The process is virtually electro-neutral however, cell 40 develops a $Na^+$ deficiency and a steep, inwardly directed $Na^+$ concentration gradient across baso-lateral membrane 30. At the same time, a steep, outwardly directed $K^+$ concentration gradient is created across baso-lateral membrane 30. The intracellular $Na^+$ deficiency created by the $Na^+K^+ATPase$ 38 of FIG. 2 provides basis for the inwardly and outwardly directed $Na^+$ and $Cl^-$ transports of FIGS. 3 and 4.

In FIG. 3, The $Na^+2Cl^-K^+$ cotransporter 42 acts in the following manner: driven by the $Na^+$ deficiency gradient, $Na^+$ ions 48, each accompanied by two $Cl^-$ ions 50 and a $K^+$ ion 52, are transported through baso-lateral membrane 30, to the inside of cell 40. Note that $Cl^-$ ions 50 and $K^+$ ions 52 are taken into cell 40 against the $K^+/Cl^-$ concentration gradient. In turn, $Cl^-$ ions 50 transport outwardly, through $Cl^-$ ion channels 51 in apical membrane 32, and $K^+$ ions 52 transport inwardly, through $K^+$ ion channels 53 in baso-lateral membrane 30, following the aforementioned $K^+/Cl^-$ concentration gradient. The result of these transports is the generation of a transepithelial potential difference wherein apical membrane 32 carries a negative charge and baso-lateral membrane 30 becomes positively charged. In response to this potential difference a flux of $Na^+$ ions 48 moves from the baso-lateral membrane 30 side to the apical membrane 32 side through paracellular spaces 36.

FIG. 4 shows, also following the $Na^+$ deficiency gradient created by $Na^+K^+ATPase$ pump 38, the inwardly directed movement of Na+ ions 56, taken into cell 40 through $Na^+$ ion channels 57 in apical membrane 32. $Na^+K^+ATPase$ 38 is shown as a continuing activity in FIG. 4 by the coupled exchange of $K^+$ ions 46 and $Na^+$ ions 44 through baso-lateral membrane 30. Thus, $Na^+$ ions 44 and 56 act as a transcellular flux, from lacrimal film 11, through apical membrane 32, and continuing through baso-lateral membrane 30 of cells 40 toward anterior chamber 18 of eye 10. The electrical effect of this movement of $Na^+$ ions 44 and 56 is an accompanying flux of $Cl^-$ ions 58 moving from the negatively charged apical membrane 32 side to the positively charged baso-lateral membrane 30 side through paracellular spaces 36.

As previously mentioned, $Na^+$ and $Cl^-$ ions in lacrimal film 11, intercellular spaces 34 and paracellular spaces 36 are surrounded by a cloud of water molecules. This cloud may include other non-ionic, water soluble molecules such as ophthalmic drugs. The direction and rate of ions leaving extracellular spaces 34 and 36 is established by the processes of FIGS. 2–4. As the ions leave extracellular spaces 34 and 36, they drag closely associated molecules along with them, into anterior chamber 18 of eye 10 by the effect known as "solvent drag".

Topical application of a loop diuretic such as furosimide or bumetanide temporarily blocks the $Na^+2Cl^-K^+$ 42 cotransporter in baso-lateral membrane 30. This brings the outward ion flow of FIG. 3 to a halt, while leaving the inward ion flow of FIG. 4 active. In this environment, a dissolved non-ionic ophthalmic drug in an aqueous solution is transported inwardly, from the lacrimal film, through the epithelium to the anterior chamber, by solvent drag. Thus, a preferred method for practicing the present invention is dispensing ophthalmic drugs such as beta blocker,, and other intraocular pressure lowering substances, or cortisone and other substances, topically, as an aqueous solution, accompanied by an aqueous solution of a loop diuretic such as furosimide, bumetanide, torasemide, ethacrynic acid, or the like. It is considered that loop diuretic concentrations between 0.001% arid 40.0% by weight should be safe and effective for the purpose of the present inventions. It is also considered that the ophthalmic drug should be dispensed in a similar concentration.

The electrochemical mechanism of the present invention can be described, in essence, as a directional reversal of the loop of Henle diuretic process well known in association with kidney function. The processes shown and described above are exemplary. Many details are often found in the art and, therefore, many such details are neither shown nor described. It is not claimed that all of the details, parts, elements, or steps described and shown were invented herein. Even though numerous characteristics and advantages of the present inventions have been described in the drawings and accompanying text, the description is illustrative only, and changes may be made in the detail, especially in matters of the order of steps and arrangement of elements within the principles of the inventions, to the full extent indicated by the broad meaning of the terms of the attached claims.

The restrictive description and drawings of the specific examples above do not point out what an infringement of this patent would be, but are to provide at least one explanation of how to use and make the inventions. The limits of the inventions and the bounds of the patent protection are measured by and defined in the following claims.

I claim:

1. A method for enhancing the penetration of an ophthalmic drug through the corneal epithelium in treating the interior of the human eye comprising the steps of:

applying a therapeutic ophthalmic drug other than a loop diuretic in aqueous solution topically to the corneal epithelium;

blocking the $Na^+2Cl^-K^+$ cotransporter of the corneal epithelium by topical application of a loop diuretic, so as to stop outwardly directed ion movement through the baso-lateral membranes of the corneal epithelium and correspondingly increase the net inwardly directed movement of ions through the corneal epithelium and into the eye interior; and taking the therapeutic ophthalmic drug into the eye interior along with the inwardly directed ion movement by the associated solvent drag.

2. A method for treating the interior of the human eye according to claim 1 wherein the topically applied loop diuretic is furosimide.

3. A method for treating the interior of the human eye according to claim 1 wherein the topically applied loop diuretic is bumetanide.

4. A method for treating the interior of the human eye according to claim 1 wherein the topically applied loop diuretic is torasemide.

5. A method for treating the interior of the human eye according to claim 1 wherein the topically applied loop diuretic is ethacrynic acid.

6. A method for enhancing the penetration of an ophthalmic drug through the corneal epithelium in treating the interior of the human eye comprising the steps of:

preparing an aqueous solution of a loop diuretic;

preparing an aqueous solution of a second ophthalmic drug other than a loop diuretic;

applying the loop diuretic solution topically to the corneal epithelium so as to block outwardly directed ion movement through the corneal epithelium baso-lateral membrane and increase the net inwardly directed ion movement through the corneal epithelium and into the eye interior; and applying the second ophthalmic drug solution topically to the corneal epithelium, so that the second ophthalmic drug is taken into the eye interior along with the inwardly directed ion movement by solvent drag.

7. A method for treating the interior of the human eye according to claim 6 wherein the topically applied loop diuretic is furosimide.

8. A method for treating the interior of the human eye according to claim 6 wherein the topically applied loop diuretic is bumetanide.

9. A method for treating the interior of the human eye according to claim 6 wherein the topically applied loop diuretic is torasemide.

10. A method for treating the interior of the human eye according to claim 6 wherein the topically applied loop diuretic is ethacrynic acid.

11. A method for enhancing the penetration of an ophthalmic drug through the corneal epithelium in treating the interior of the human eye comprising the steps of:

preparing an aqueous solution of a loop diuretic and a second ophthalmic drug other than a loop diuretic;

applying the solution topically to the corneal epithelium so as to block outwardly directed ion movement through the baso-lateral membrane of the corneal epithelium and increase the net inwardly directed ion movement through the corneal epithelium and into the eye interior; and applying the second ophthalmic drug solution topically to the corneal epithelium, so that the second ophthalmic drug is taken into the eye interior along with the inwardly directed ion movement.

12. A method for treating the interior of the human eye according to claim 11 wherein the topically applied loop diuretic is furosimide.

13. A method for treating the interior of the human eye according to claim 11 wherein the topically applied loop diuretic is bumetanide.

14. A method for treating the interior of the human eye according to claim 11 wherein the topically applied loop diuretic is torasemide.

15. A method for treating the interior of the human eye according to claim 11 wherein the topically applied loop diuretic is ethacrynic acid.

16. A method for treating the eye by improved transportation of a therapeutic ophthalmic drug through corneal epithelium and into the anterior chamber, comprising the steps of:

preparing an aqueous solution containing between 0.001% and 40% of a diuretic chosen from a group including furosimide, bumetanide, torasemide and ethacrynic acid;

applying the first aqueous solution topically to the cornea of the eye to be treated;

preparing a second aqueous solution containing between 0.001% and 40% of the therapeutic ophthalmic drug; and applying the second aqueous solution topically to the cornea of the eye to be treated.

* * * * *